(12) United States Patent
Hua et al.

(10) Patent No.: US 10,952,964 B2
(45) Date of Patent: *Mar. 23, 2021

(54) TARGETED DELIVERY OF DRUGS TO THE MYOMETRIUM VIA POLYPEPTIDES THAT BIND TO THE OXYTOCIN RECEPTOR

(71) Applicant: The University of Newcastle, Callaghan (AU)

(72) Inventors: Susan Hua, Charlestown (AU); Jonathan Paul, Cardiff (AU); Roger Smith, Newcastle (AU)

(73) Assignee: The University of Newcastle, Callaghan (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/435,061

(22) Filed: Jun. 7, 2019

(65) Prior Publication Data

US 2019/0290584 A1 Sep. 26, 2019

Related U.S. Application Data

(63) Continuation of application No. 14/892,927, filed as application No. PCT/AU2014/050049 on May 23, 2014, now Pat. No. 10,350,167.

(30) Foreign Application Priority Data

May 23, 2013 (AU) ................................ 2013901842

(51) Int. Cl.
| | | |
|---|---|---|
| *A61K 9/127* | (2006.01) | |
| *A61K 31/137* | (2006.01) | |
| *A61K 31/18* | (2006.01) | |
| *A61K 31/4015* | (2006.01) | |
| *A61K 31/4422* | (2006.01) | |

(52) U.S. Cl.
CPC .......... *A61K 9/1271* (2013.01); *A61K 31/137* (2013.01); *A61K 31/18* (2013.01); *A61K 31/4015* (2013.01); *A61K 31/4422* (2013.01)

(58) Field of Classification Search
None
See application file for complete search history.

(56) References Cited

U.S. PATENT DOCUMENTS

| | | |
|---|---|---|
| 5,536,241 A | 7/1996 | Zapol |
| 6,310,050 B1 | 10/2001 | Advenier et al. |
| 6,316,024 B1 | 11/2001 | Allen et al. |
| 2005/0049255 A1 | 3/2005 | Bictash et al. |
| 2016/0113872 A1 | 4/2016 | Hua et al. |

FOREIGN PATENT DOCUMENTS

WO 2013075176 A1 5/2013

OTHER PUBLICATIONS

Bardou et al., Pharmacological and biochemical study on the effects of selective phosphodiesterase inhibitors on human term myometrium. Naunyn-Schmiedeberg's Arch. Pharmacol., 360, 457-463, 1999. (Year: 1999).*
Bennett, P, Letter to The Australian Museum Eureka Prize Committee, from Professor Phillip Bennett, 2 pages, May 1, 2017.
Daftary, G, et al., "Efficient Liposome-Mediated Gene Transfection and Expression in the Intact Human Uterus", Human Gene Therapy 12, 2121-2127 (2001).
Fahmy, et al., "Targeted for drug delivery", Materials Today 8(8), 18-26 (2005).
Huszar, et al., "Biochemistry and pharmacology of the myometrium and labor: Regulation at the cellular and molecular levels", Am J Obstet Gynecol 142, 225-237 (1982).
Kannan, R, et al., "Emerging nanomedicine approaches in obstetrics", American Journal of Obstetrics Gynecology 201-203 (2017).
Macones, G, et al., "The controversy surrounding indomethacin for tocolysis", Am J Obstet Gynecol 184(3), 264-272 (2001).
Mohan, A, et al., "Drugs acting on the pregnant uterus", Curr Obstet & Gynecol 16, 174-180 (2006).
Patent Cooperation Treaty, International Search Report dated Oct. 3, 2014, issued in counterpart application No. PCT/AU2014/050049 (4 pages).
Patent Cooperation Treaty, International Written Opinion dated Oct. 3, 2014, issued in counterpart application No. PCT/AU2014/050049 (7 pages).
Paul, J, Letter from Society for Reproductive Investigation to Dr. Paul regarding Abstract O-003, A Targeted Drug Delivery System for the Uterus, selected for oral presentation, 1 page, Jan. 12, 2015.
Paul, J, et al., "Drug delivery to the human and mouse uterus using immunoliposomes targeted to the oxytocin receptor", American Journal of Obstetrics & Gynecology 283.e1-283.e14 (2017).
Refuerzo, J, et al., "Targeted nanoparticles in pregnancy: a new frontier in perinatal therapeutics", American Journal of Obstetrics & Gynecology 204-205 (2017).
Zeeman, et al., "Oxytocin and its receptor in pregnancy and parturition: Current concepts and clinical implications", Obstetrics and Gynecology 89, 873-883 (1997).
Dennis, A, et al., "Acute pulmonary oedema in pregnant women", Anaesthesia 67, 646-659 (2012).
Norton, M, et al., "Neonatal Complications After the Administration of Indomethacin for Preterm Labor", The New Englad Journal of Medicine 329(22), 1602-1607 (1993).
Rosenecker, J, et al., "Increased liposome extravasation in selected tissues: Effect of substance P", Proc Natl Acad Sci 93, 7236-7241 (1996).
Wilhelm, S, et al., "Analysis of nanoparticle delivery to tumours", Nature Reviews 1, 1-12 (2016).

\* cited by examiner

*Primary Examiner* — Elly-Gerald Stoica
(74) *Attorney, Agent, or Firm* — Viksnins Harris Padys Malen LLP (57) ABSTRACT

Provided herein are methods and compositions for the targeted delivery to myometrial tissue of one or more agents capable of regulating contractility of myometrial tissue, wherein the one or more agents are contained or encapsulated within a polymeric delivery vehicle conjugated with one or more molecules that recognizes and/or is capable of binding, directly or indirectly, to the oxytocin receptor.

8 Claims, 7 Drawing Sheets

TARGETED DELIVERY OF DRUGS TO THE MYOMETRIUM VIA POLYPEPTIDES THAT BIND TO THE OXYTOCIN RECEPTOR

CROSS-REFERENCE TO RELATED APPLICATIONS

This application is a continuation of U.S. application Ser. No. 14/892,927, which is a 35 U.S.C. § 371 Application of International Application No. PCT/AU2014/050049, filed May 23, 2014, the disclosure of which is incorporated by reference, and claims priority to Australian Application No. 2013901842, filed May 23, 2013.

FIELD OF THE DISCLOSURE

The present disclosure relates generally to methods and compositions for targeting drugs to the myometrium to ensure that drugs having action on myometrial tissue, for example in regulating uterine contractions, are delivered to the desired site of action, thereby minimising or eliminating off-target effects.

BACKGROUND

Contractility of the myometrium, the smooth muscle layers of the uterus, is essential for the normal progression of human pregnancy and the initiation of labour. The onset of labour is associated with increasing frequency and intensity of uterine contractions, tightening the uterus and pushing the baby from the uterus into the birth canal for delivery.

A common complication of pregnancy and labour is inadequate uterine contractions. This can lead to a delay or failure in the initiation of labour or to abnormally prolonged and difficult labour (dystocia). Dystocia can result in an assisted delivery (including forceps delivery or Caesarean section) and may result in fetal health complications such as respiratory or nerve damage, or even fetal death.

In contrast, the initiation, or increase in intensity or frequency, of uterine contractions too early in pregnancy can lead to premature labour and premature or preterm birth (defined as less than 37 weeks gestational age). Preterm birth is associated with a significant increase in infant morbidity and mortality, and places an enormous burden not only on parents but on the health system. The management of premature labour is of critical importance.

Thus, during pregnancy the timing onset and maintenance of uterine contractions is critical for the normal progression of labour and there are circumstances in which it is desirable or necessary to intervene to regulate uterine contractions (either induce or stimulate uterine contractions to avoid prolonged labour, or reduce the frequency and/or intensity of uterine contractions to avoid premature labour).

Myometrial contractility is also critical after childbirth. Following the separation of the placenta from the uterine wall, blood flow is slowed in the uterus by persistent, regular myometrial contractions. With increased clotting proteins present and blood flow slowed by uterine contractions, myometrial arteries clot. Uterine contractions following birth are generally sufficient to slow the velocity of blood flowing through the uterus to initiate blood clot formation throughout myometrium. However in some women uterine contractions are inadequate. Uncontrolled bleeding following childbirth (post partum haemorrhage) can result in significant blood loss having major health implications for the new mother and even resulting in death.

Intense uterine contractions during the menstrual cycle in non-pregnant females can also be the cause of severe pain and cramping (dysmenorrhoea).

Several types or classes of drugs are presently available either to stimulate myometrial contractility (contractile drugs) or to inhibit or reduce myometrial contractility (relaxatory drugs), however use of these drugs is typically associated with side effects beyond the uterus, most notably in the cardiovascular system, and may be contraindicated in sufferers of hypertension or hypotension. Indeed several drugs that have proved to be effective in regulating uterine contractions, such as salbutamol, have fallen out of favour and have ceased to be used due to these off-target effects.

The present inventors have now developed means of targeting drugs to the myometrium such that the appropriate drug dose is available within the uterus to have the desired effect on uterine contractions while avoiding the exposure of other parts of the body to the potentially damaging side effects of the drugs. The present invention therefore not only provides a novel means for the targeted delivery of any drug(s) to the myometrium, but also provides the opportunity to continue employment of drugs that may have systemic or other off-target side effects, including drugs the use of which in relation to the myometrium has previously ceased, thereby potentially reducing the need for the development of new drugs or other therapies.

SUMMARY

According to a first aspect disclosed herein there is provided a method for targeted delivery to myometrial tissue of one or more agents capable of regulating contractility of said myometrial tissue, wherein the one or more agents are conjugated, either directly or indirectly, to one or more molecules recognizing and/or capable of binding, directly or indirectly, to the oxytocin receptor.

In a particular embodiment the one or more agents are contained or encapsulated within a polymeric delivery vehicle conjugated with one or more molecules recognizing and/or capable of binding, directly or indirectly, to the oxytocin receptor.

The polymeric delivery vehicle may be a liposome. In a particular embodiment the polymeric delivery vehicle may be conjugated with anti-oxytocin receptor antibodies. The polymeric delivery vehicle may be coated with the anti-oxytocin receptor antibodies. The antibodies may be polyclonal or monoclonal antibodies. In an exemplary embodiment, the antibodies bind to an extracellular domain of the oxytocin receptor.

In a particular embodiment the one or more agents may stimulate or induce contractility of the myometrial tissue. In accordance with this embodiment, exemplary agents include potassium channel inhibitors. For example, the potassium channel inhibitor may be dofetilide or E-4031.

In an alternate embodiment the one or more agents inhibit or reduce contractility of the myometrial tissue. In accordance with this embodiment, exemplary agents include calcium channel inhibitors, $\beta_2$-adrenergic receptor agonists and phosphodiesterase inhibitors. By way of example only, the calcium channel inhibitor may be nifedipine. By way of example only, the $\beta_2$-adrenergic receptor agonist may be salbutamol or ritodrine. By way of example only, the phosphodiesterase inhibitor may be rolipram.

According to a second aspect disclosed herein there is provided a method for regulating contractility of myometrial tissue, the method comprising exposing the myometrial tissue to an effective amount of one or more agents capable of regulating contractility of said myometrial tissue, wherein the one or more agents are conjugated, either directly or indirectly, to one or more molecules recognizing and/or capable of binding, directly or indirectly, to the oxytocin receptor.

In a particular embodiment the one or more agents are contained or encapsulated within a polymeric delivery vehicle conjugated with one or more molecules recognizing and/or capable of binding, directly or indirectly, to the oxytocin receptor.

The polymeric delivery vehicle may be a liposome. In a particular embodiment the polymeric delivery vehicle may be conjugated with anti-oxytocin receptor antibodies. The polymeric delivery vehicle may be coated with the anti-oxytocin receptor antibodies. The antibodies may be polyclonal or monoclonal antibodies. In an exemplary embodiment, the antibodies bind to an extracellular domain of the oxytocin receptor.

In a particular embodiment the one or more agents may directly or indirectly stimulate or induce contractility of the myometrial tissue. The agent(s) may be potassium channel inhibitors. The potassium channel inhibitor may be dofetilide or E-4031.

In an alternate embodiment the one or more agents may directly or indirectly inhibit or reduce contractility of the myometrial tissue. The agent(s) may be selected from calcium channel inhibitors, $\beta_2$-adrenergic receptor agonists and phosphodiesterase inhibitors. By way of example only, the calcium channel inhibitor may be nifedipine. By way of example only, the $\beta_2$-adrenergic receptor agonist may be salbutamol or ritodrine. By way of example only, the phosphodiesterase inhibitor may be rolipram. Further by way of example the agent may inhibit prostaglandin production or function in the myometrium, such as cyclooxygenase inhibitors and phospholipase A2 inhibitors.

In accordance with the above aspects and embodiments the liposomes may be administered to a female mammal. The female mammal may be pregnant, may be in labour or may have given birth.

In one embodiment the female mammal is pregnant and the administration provided to stimulate uterine contractions and thereby induce or assist labour. Accordingly, the administration may be for the treatment or prevention of dystocia.

In another embodiment the female mammal is pregnant and the administration is provided to reduce or inhibit uterine contractions and thereby slow down labour or prevent premature labour.

In another embodiment the administration is provided to stimulate uterine contractions post labour to inhibit blood loss.

In another embodiment the administration is for the treatment or prevention of dysmenorrhea.

In a third aspect disclosed herein there is provided a composition for carrying out a method according to the first or second aspect, the composition comprising one or more agents capable of regulating contractility of myometrial tissue wherein the one or more agents are conjugated, directly or indirectly, with one or more molecules recognizing and/or capable of binding, directly or indirectly, to the oxytocin receptor, and one or more pharmaceutically acceptable carriers, diluents or excipients.

In particular embodiments, the composition comprises one or more agents capable of regulating contractility of myometrial tissue contained or encapsulated within a polymeric delivery vehicle, wherein the polymeric delivery vehicle is conjugated with one or more molecules recognizing and/or capable of binding, directly or indirectly, to the oxytocin receptor, and one or more pharmaceutically acceptable carriers, diluents or excipients.

Also disclosed herein is the use of a polymeric delivery vehicle encapsulating one or more agents capable of regulating contractility of myometrial tissue, wherein the polymeric delivery vehicle is conjugated with one or more molecules recognizing and/or capable of binding, directly or indirectly, to the oxytocin receptor, for the manufacture of a medicament.

BRIEF DESCRIPTION OF THE DRAWINGS

Aspects and embodiments disclosed and exemplified herein are illustrated, by way of non-limiting example only with reference to the following drawings.

DETAILED DESCRIPTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method step or group of elements or integers or method steps.

As used in the subject specification, the singular forms "a", "an" and "the" include plural aspects unless the context clearly dictates otherwise. Thus, for example, reference to "an agent" includes a single agent, as well as two or more agents; reference to "the disclosure" includes a single and multiple aspects described in the disclosure; and so forth. All aspects disclosed, described and/or claimed herein are encompassed by the term "invention". Such aspects are enabled across the width of the present invention.

The terms "agent", "pharmacologically active agent", "medicament" and "drug" may be used interchangeably herein. These terms also encompass pharmaceutically acceptable and pharmacologically active ingredients of those agents mentioned herein, including, but not limited to, salts, esters, amides, prodrugs, active metabolites, analogs, mimetics functional equivalents and the like.

The term "inhibiting" and variations thereof as used herein do not necessarily imply the complete inhibition of myometrial contractility or uterine contractions. Rather, the inhibition may be to an extent, and/or for a time, sufficient to produce the desired effect. Such inhibition may be in magnitude and/or be spatial or temporal in nature. In particular contexts, the terms "inhibit" and "prevent", and variations thereof may be used interchangeably.

As used herein the terms "treating", "treatment", "preventing" and "prevention" refer to any and all uses which remedy a disease, disorder or condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. Similarly, "prevention" does not necessarily mean that the subject will not eventually contract a particular disease, disorder or condition. Rather, "prevention" encompasses reducing the severity of, or delaying the onset of, a particular disease, disorder or condition. In the context of some conditions, methods of the present invention involve "treating" the disease, disorder or condition in terms of reducing or eliminating the occurrence of a highly undesirable and irreversible outcome of the progression of the condition but may not of itself prevent the initial occurrence of the disease, disorder or condition. Accordingly, treatment and prevention include amelioration of the symptoms of a particular disease, disorder or condition or preventing or otherwise reducing the risk of developing a particular disease, disorder or condition.

As used herein the terms "effective amount" and "effective dose" include within their meaning a non-toxic but sufficient amount or dose of an agent or compound to provide the desired effect. The exact amount or dose required will vary from subject to subject depending on factors such as the species being treated, the age and general condition of the subject, the severity of the disease, disorder or condition being treated, the particular agent being administered and the mode of administration and so forth. Thus, it is not possible to specify an exact "effective amount" or "effective dose". However, for any given case, an appropriate "effective amount" or "effective dose" may be determined by one of ordinary skill in the art using only routine experimentation. In some embodiments, an effective amount for a human subject lies in the range of about 0.1 ng/kg body weight/dose to 1 g/kg body weight/dose. In some embodiments, the range is about 1 μg to 1 g, about 1 mg to 1 g, 1 mg to 500 mg, 1 mg to 250 mg, 1 mg to 50 mg, or 1 μg to 1 mg/kg body weight/dose. Dosage regimes are adjusted to suit the exigencies of the situation and may be adjusted to produce the optimum therapeutic dose. For example, several doses may be provided daily, weekly, monthly or other appropriate time intervals.

The term "subject" as used herein refers to a mammal, typically a human. However, it will be understood by those skilled in the art that aspects disclosed herein have both human and veterinary applications, and hence both human and non-human mammals may benefit from the compositions and methods herein disclosed. Thus in the context of the present disclosure "subject" includes livestock and companion animals such as cattle, horses, sheep, pigs, camelids, goats, donkeys, dogs and cats. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates. A "subject" may also be referred to in the present disclosure as an individual, patient, or recipient.

Disclosed herein are methods for targeted delivery to myometrial tissue of one or more agents capable of regulating contractility of said myometrial tissue, wherein the one or more agents are conjugated, directly or indirectly, with one or more molecules recognizing and/or capable of binding, directly or indirectly, to the oxytocin receptor.

Also disclosed herein are methods for regulating contractility of myometrial tissue, the method comprising exposing the myometrial tissue to an effective amount of one or more agents capable of regulating contractility of said myometrial tissue, wherein the one or more agents are conjugated, directly or indirectly, with one or more molecules recognizing and/or capable of binding, directly or indirectly, to the oxytocin receptor.

It may, for example, be advantageous to induce uterine contractions in a pregnant mammal in order to induce or assist labour where the pregnancy is difficult, complicated or abnormal in some way and continuing the pregnancy may jeopardise the health of mother and/or child. It may also be advantageous to induce uterine contractions in a pregnant mammal in order to induce labour where the pregnancy has already reached term or is post-term. As used herein, the term dystocia refers to any difficult or obstructed labour, or labour progressing abnormally slowly, including for example shoulder dystocia or a prolonged second stage of labour. Inducing uterine contractions may also be necessary after delivery to minimise blood loss and prevent or reduce post partum hemorrhaging.

It may be advantageous to inhibit or reduce uterine contractions in a pregnant mammal, in frequency and/or in intensity, in order to slow down labour, for example in order to prevent or minimise the risk that the pregnant mammal will enter premature labour, or where the pregnant mammal is already in premature labour, to prevent or minimise the risk of preterm birth.

Also enabled herein are pharmaceutical compositions for use in accordance with the disclosed methods, the compositions comprising one or more agents capable of regulating contractility of myometrial tissue wherein the agents are conjugated, directly or indirectly, with one or more molecules recognizing and/or capable of binding, directly or indirectly, to the oxytocin receptor, and one or more pharmaceutically acceptable carriers, diluents or excipients.

In accordance with the present invention the delivery of agents to myometrial tissue by conjugation, directly or indirectly, with one or more molecules recognizing and/or capable of binding, directly or indirectly, to the oxytocin receptor does not involve conjugation (directly or indirectly) of the agent(s) to the oxytocin peptide. As such the present invention avoids problems associated with the linking of oxytocin to pharmaceutically active drugs, including (but not limited to) the constraints placed on the nature and size of the pharmaceutically active drugs that can be linked to the small oxytocin peptide without disrupting the structure and/or function of oxytocin or its ability to recognise and bind the oxytocin receptor. Rather the present inventors have developed a novel approach to the targeting of pharmaceutically active drugs to myometrial tissue that enables any drug to be specifically targeted, regardless of nature or size and which enables any number of drugs to be delivered in combination.

In accordance with particular embodiments of the present disclosure, the agents to be delivered to the myometrium are contained in a polymeric delivery vehicle capable of holding and delivering the required agent or agents to the myometrium and capable of binding, either directly, or indirectly, the oxytocin receptor expressed on the surface of myometrial cells. Typically the delivery vehicle encapsulates the agent or agents. By way of example, the delivery vehicle may comprise liposomes, or other liposome-like compositions such as micelles (e.g. polymeric micelles), lipoprotein-based drug carriers, nanoparticles, or dendrimers. In particular exemplary embodiments, the delivery vehicle comprises liposomes.

Liposomes are typically characterized by having an interior space sequestered from an outer medium by a membrane of one or more lipid-containing bilayers. In accordance with the present invention, an agent(s) to be delivered using liposomes (or other liposome-like compositions) is contained in or encapsulated within the liposome or liposome-like composition. Those skilled in the art will appreciate that by "contained" is meant that the agent(s) may be completely or partially located in the interior space of the liposome or liposome-like composition, within the bilayer membrane of the liposome or liposome-like composition, or associated with the exterior surface of the membrane. Liposome-forming components are well known to those skilled in the art and include, by way of example only, DMPC, DMPG, DSPC, DOPC, DPPG, DSPG, HSPC, cholesterols, egg phospholipids and soy phospholipids, and mixtures thereof.

Targeted delivery of agents disclosed herein to the myometrium is typically achieved by modifying such delivery vehicles by the addition of ligands to vehicle surfaces, suitable ligands including polypeptides, peptides, antibodies and lectins, that enable increased target specificity. Thus agents disclosed herein may be encapsulated within, or otherwise linked with liposome, micelle, lipoprotein-based drug carrier, nanoparticle, and dendrimer based delivery vehicles which can then in turn be coated or conjugated with a molecule or compound capable of interacting with oxytocin receptors in the myometrium. Suitable molecules and compounds for use in this regard include, but are not limited to antibodies that bind oxytocin receptors. The antibody may be specific or selective for an oxytocin receptor. Alternatively, agents disclosed herein may be directly conjugated with a compound capable of interacting with oxytocin receptors in the myometrium such as an oxytocin receptor-binding antibody.

Agents and compositions disclosed herein may be administered via any convenient or suitable route such as by parenteral, oral, or topical routes. In particular embodiments intra-uterine delivery of the agent or composition may be advantageous. A variety of suitable intra-uterine drug delivery devices or systems are available and would be known to those skilled in the art, including for example, those described in Wildemeersch et al. (2003) and Wildemeersch (2010), the disclosures of which are incorporated herein by reference.

Those skilled in the art will recognise that a variety of drugs may be administered to the myometrium in accordance with the present disclosure, and the scope of this disclosure should not be limited by reference to any particular drugs. Typically the drug is an agent capable of effecting contractility of myometrial tissue.

In particular embodiments the agent is capable of, directly or indirectly, stimulating or inducing myometrial contractility. By way of example only, suitable agents for use in such embodiments include potassium channel inhibitors or blockers, such as dofetilide and E-4031. However those skilled in the art will appreciate that the scope of suitable agents is not so limited, and any agent capable of stimulating or inducing myometrial contractility may be employed. Those skilled in the art will also appreciate that multiple drugs may be combined and administered in accordance with the present disclosure.

In particular embodiments the agent is capable of, directly or indirectly, relaxing myometrial tissue and thereby reducing or inhibiting myometrial contractility. By way of example only, suitable agents for use in such embodiments include calcium channel inhibitors or blockers, $\beta_2$-adrenergic receptor agonists and phosphodiesterase inhibitors. Exemplary calcium channel blockers include nifedipine. Exemplary $\beta_2$-adrenergic receptor agonists include salbutamol and ritodrine. Exemplary phosphodiesterase inhibitors include rolipram. Exemplary agents that may be used to indirectly inhibit myometrial contractility include inhibitors of prostaglandin production or function, including cyclooxygenase inhibitors and phospholipase A2 inhibitors. However those skilled in the art will appreciate that the scope of suitable agents is not so limited, and any agent capable of relaxing myometrial tissue and reducing or inhibiting myometrial contractility may be employed. Those skilled in the art will also appreciate that multiple drugs may be combined and administered in accordance with the present disclosure.

Pharmaceutical compositions disclosed herein may comprise one or more pharmaceutically acceptable carriers, diluents or excipients.

By pharmaceutically acceptable carrier, diluent or excipient is meant a pharmaceutical vehicle comprised of a material that is not biologically or otherwise undesirable, i.e. the material may be administered to a subject along with the selected conjugate without causing any or a substantial adverse reaction. Carriers may include excipients and other additives such as diluents, detergents, colouring agents, wetting or emulsifying agents, pH buffering agents, preservatives, and the like. Carriers may also include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The pharmaceutical compositions disclosed herein may conveniently be presented in unit dosage form and may be prepared according to conventional techniques well known in the pharmaceutical industry. Such techniques include the step of bringing into association the active agent(s) with the pharmaceutical carrier(s) or excipient(s). The compositions described herein may be formulated into any of many possible dosage forms such as, but not limited to, injectable formulations, and tablets, capsules, gel capsules and liquids. Accordingly, pharmaceutical compositions described herein include, but are not limited to, solutions, emulsions, foams and liposome-containing formulations. The pharmaceutical compositions and formulations herein described may comprise one or more penetration enhancers, carriers, excipients or other active or inactive ingredients.

Pharmaceutical forms suitable for injectable use include sterile aqueous solutions (where water soluble) or dispersions and sterile powders for the extemporaneous preparation of sterile injectable solutions or dispersions. The formulation must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filter sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

Tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present disclosure further contemplates combination therapies, wherein agents disclosed herein are coadministered with other suitable agents that may effect myometrial contractility, uterine contractions or otherwise assist in providing for the normal progression of labour in some other way. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. In sequential administration the molecules or compounds may be administered in any order.

Those skilled in the art will appreciate that aspects described herein are susceptible to variations and modifications other than those specifically described. It is to be understood that these aspects include all such variations and modifications. The disclosure also includes all of the steps, features, compositions and compounds referred to or indicated in this specification, individually or collectively, and any and all combinations of any two or more of the steps or features.

Aspects taught herein are now described with reference to the following specific examples, which should not be construed as in any way limiting the scope of the invention.

EXAMPLES

Example 1—Immunoliposome Preparations and Effect on Myometrial Tissue

Liposomes composed of 1,2-distearoyl-sn-glycero-2-phosphocholine (DSPC) and cholesterol (molar ratio 2:1) containing 1,2-distearoyl-sn-glycero-3-phosphoethanolamine-N-[maleimide(polyethylene glycol)-2000 (DSPE-PEG (2000) Maleimide) at 1.5 mol percent of DSPC as a coupling lipid were prepared by dried lipid film hydration in PBS buffer. Where liposomes were loaded with a drug (see Example 2), the drug concentration was 4 mg/mL.

The resulting multilamellar dispersions were reduced in size and lamellarity by high pressure extrusion. The activated liposome suspensions were mixed with thiolated antibody prepared by conjugating oxytocin receptor (OTR) ligand antibodies (25 μg) or non-specific rabbit IgG (25 μg) with a heterobifunctional reagent N-succinimidyl-3-(2-pyridyldithio) propionate (SPDP). The anti-OTR antibody was a rabbit polyclonal antibody (Sapphire Bioscience Pty Ltd) directed against a synthetic peptide corresponding to the N-terminal extracellular domain of the human oxytocin receptor.

Excess SPDP was removed through a PD-10 column. Fractions containing pyridyldithiopropionated-Ab (PDP-Ab) conjugates (assessed by absorbance in 280 nm) were pooled and lyophilized to form a solid product, which was then stored at 40° C. under nitrogen gas. To produce thiolated-Ab (Ab-SH), PDP-Ab was reduced with 5 mM tris(2-carboxyethyl) phosphine hydrochloride (TCEP) for 5 min. Absorbance was checked at 280 nm (protein concentration) and 343 nm (SPDP modification), in order to ensure stability of the compound. The Ab-SH was mixed immediately with liposomes and incubated.

Unconjugated Ab was removed by size exclusion chromatography which excludes liposomes in the void volume. The size distribution of the liposomal dispersion was determined by dynamic laser light scattering. Finally, liposomes were then purified of any free-floating drug through centrifugal filtration through a 100,000 kDa molecular weight filter (Millipore). Free-floating drug passed through the filter (into the filtrate) whilst liposomes were collected in retentate. The retentate was washed twice with 5 mL PBS and re-centrifuged after each wash. The liposome retentate was then collected and resuspended in PBS to the original volume. Purified liposomes were then applied to contracting myometrial strips.

Figure 1A:
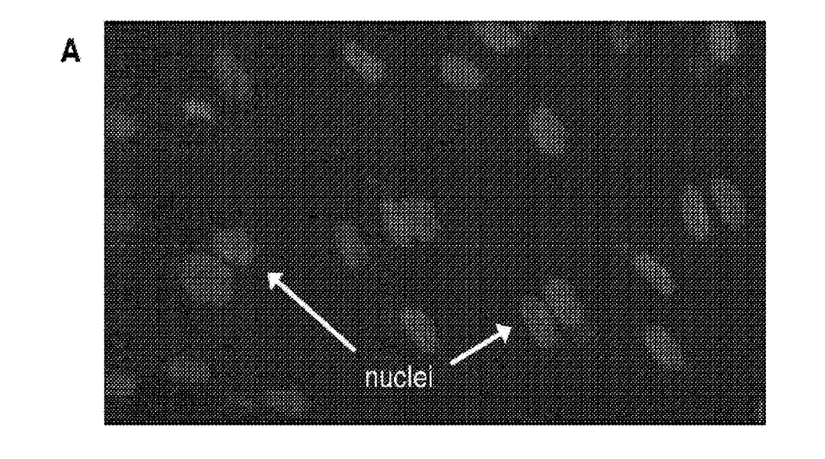
FIGS. 1A-1B. Images of hTERT-immortalised myometrial cells treated with 50 µl of either: (1A) non-targeted liposomes labelled with DiI; or (1B) liposomes labelled with DiI, the liposomes conjugated to anti-oxytocin receptor antibodies targeting the liposomes to the myometrial cells. Nuclei of cells were stained with DAPI.
Figure 1B:
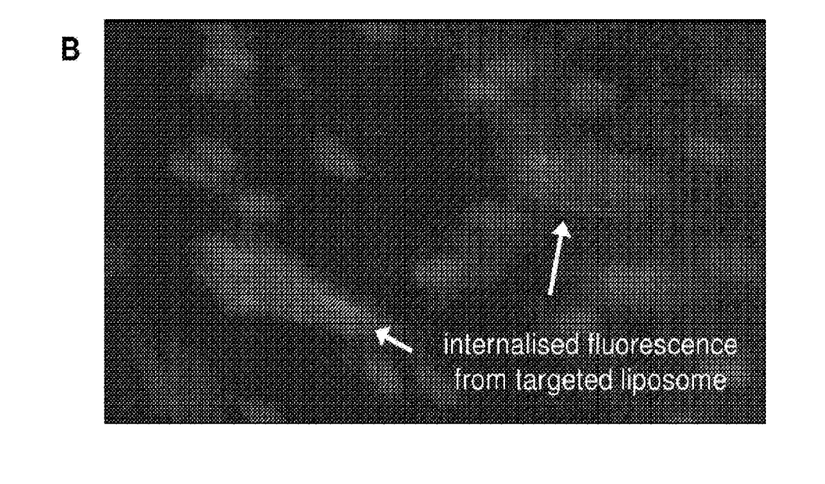

First, 50 μl OTR-targeted liposomes labelled with DiI were added to hTERT-immortalised myometrial cells in culture. As shown in FIG. 1, treatment of hTERT-immortalised myometrial cells with non-targeted liposomes revealed no internalised DiI labeling (FIG. 1A), whereas treatment with OTR-targeted liposomes revealed internalised DiI fluorescence (FIG. 1B).

Next, the effect on myometrial contractility of OTR-targeted liposomes, absent any drug loading, was examined. Myometrial samples from non-labouring women were cut into strips (7×2×2 mm) and suspended in organ baths containing 30 ml Krebs-Henseleit buffer with 1.89 mM $CaCl_2$. Strips were connected to a Grass FT03C force transducer (Grass Instruments, Quincy, Mass.) and 1 g passive tension applied. Buffer was replaced five times during the first hour, with strips re-tensioned to 1 g passive tension following each wash. Thereafter strips were maintained at 37° C. (pH 7.4) and continuously bubbled with 95% $O_2$/5% $CO_2$ until spontaneous rhythmic contractions developed. Data were digitized using a Maclab8E data-acquisition system and contraction status visualised in real time using Chart software (ADI, Melbourne, Australia). Strips were monitored for the development of spontaneous contractions. Contraction baselines were established demonstrating rhythmic contractions with consistent frequency and amplitude.

Once a contraction baseline was established tissue strips were treated by administering desired volumes liposome preparations into the organ baths. To administer the liposomes, 600 μL of KREBS buffer was carefully removed from an organ bath and transferred to a 1.5 mL Eppendorf tube. The appropriate volume of desired liposome preparation was then pipetted into the Eppendorf tube to pre-dilute the liposomes into KREBS buffer. The total volume of KREBS buffer+liposomes was then carefully re-injected back into the appropriate organ bath to administer the treatment to the myometrial strip.

Figure 2:
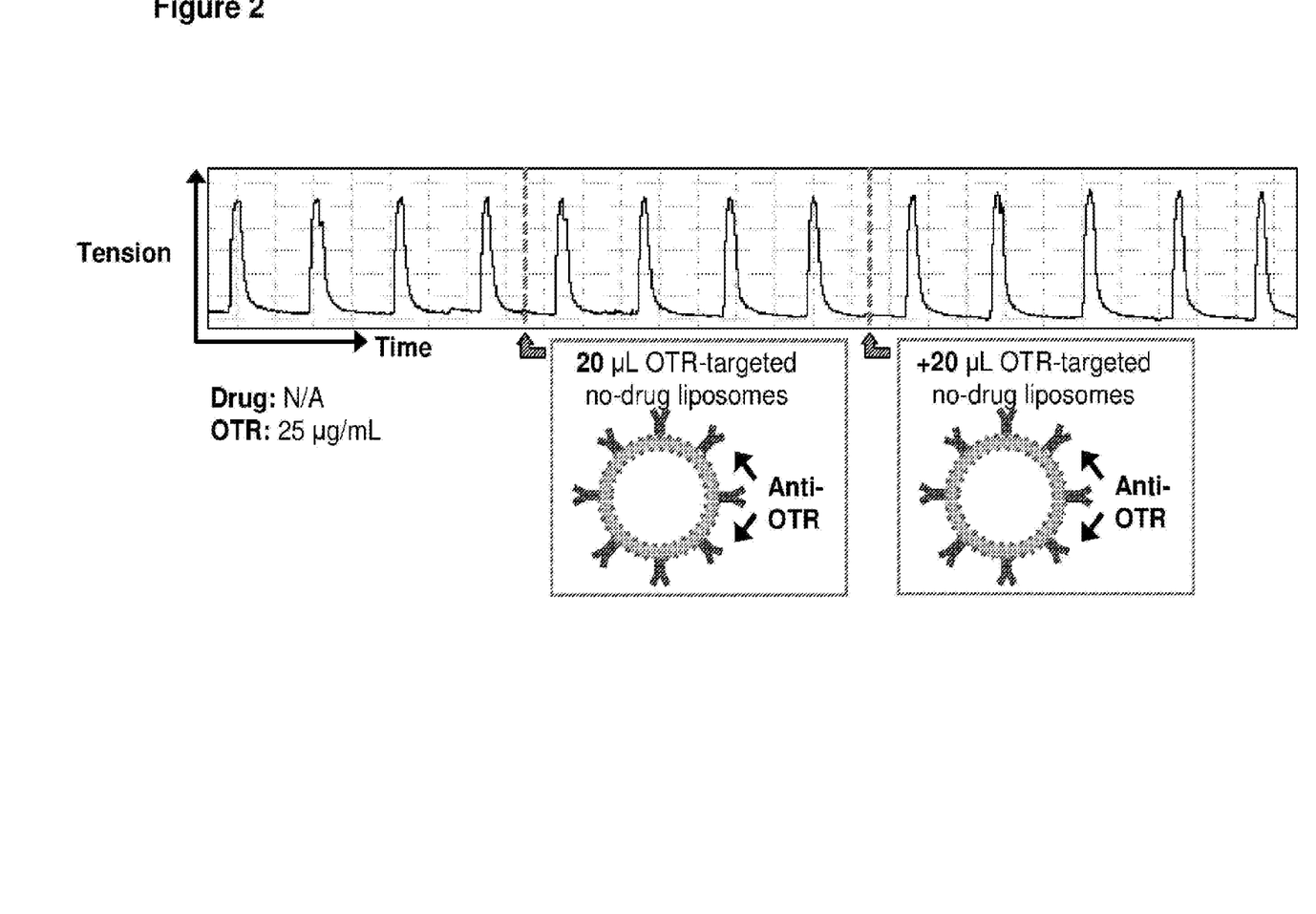
FIG. 2. Time course in spontaneously contracting human myometrial strips treated with 20 µL liposomes conjugated to anti-oxytocin receptor (OTR) antibodies, the wherein the liposomes contain no drug(s).

As shown in FIG. 2, OTR-targeted liposomes with no drug encapsulated had no effect on myometrial contractility, following two administrations (each of 20 μl) of OTR-targeted, drug free liposomes.

Example 2—Targeted Delivery of Drugs to Myometrial Cells

Having successfully demonstrated that liposomes can be targeted to bind to myometrial cells, and that these OTR-targeted liposomes alone have no effect on myometrial contractility (FIGS. 1 and 2), the inventors then examined the effect of targeted delivery to myometrial cells of a variety of drugs known to either stimulate myometrial contractility (dofetilide) or relax myometrial cells (nifedipine, salbutamol and rolipram). The liposomes were prepared as described in Example 1. The drugs were each encapsulated individually into the liposomes during preparation as per Example 1, at a concentration of 4 mg/mL. For each drug liposomes were either conjugated to the anti-OTR antibodies or to IgG antibodies. The treatment of myometrial strips using the drug-loaded liposomes was also carried out, and contractility measured, as described in Example 1.

Figure 3:
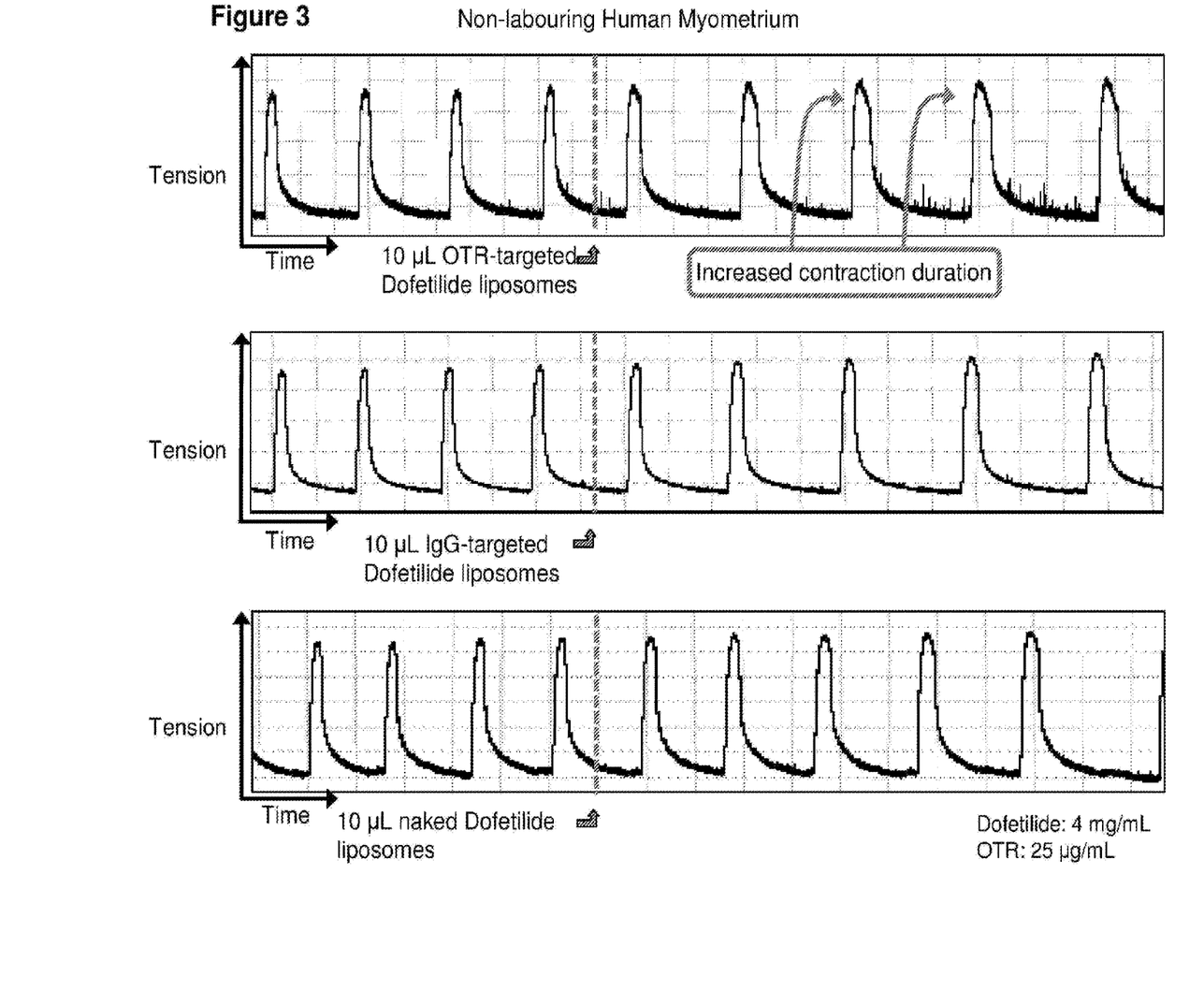
FIG. 3. Time course in spontaneously contracting human myometrial strips treated with: top panel, 10 µL liposomes conjugated to anti-oxytocin receptor (OTR) antibodies and loaded with 4 mg/mL dofetilide (DOF); middle panel, 10 µL liposomes conjugated with IgG antibodies and loaded with 4 mg/mL dofetilide; and bottom panel, 10 µL naked liposomes loaded with 4 mg/mL dofetilide.

10 μl of dofetilide-loaded OTR-liposomes were added to spontaneously contracting human myometrial strips and contractility measured. As shown in FIG. 3 (top panel), treatment with these OTR-targeted liposomes increased the duration of contractions. In contrast, treatment with dofetilide-loaded IgG-targeted liposomes (FIG. 3, middle panel) and dofetilide-loaded liposomes with no antibody coating or conjugation ('naked' liposomes; FIG. 3, bottom panel) had no effect on contraction duration.

Figure 4:
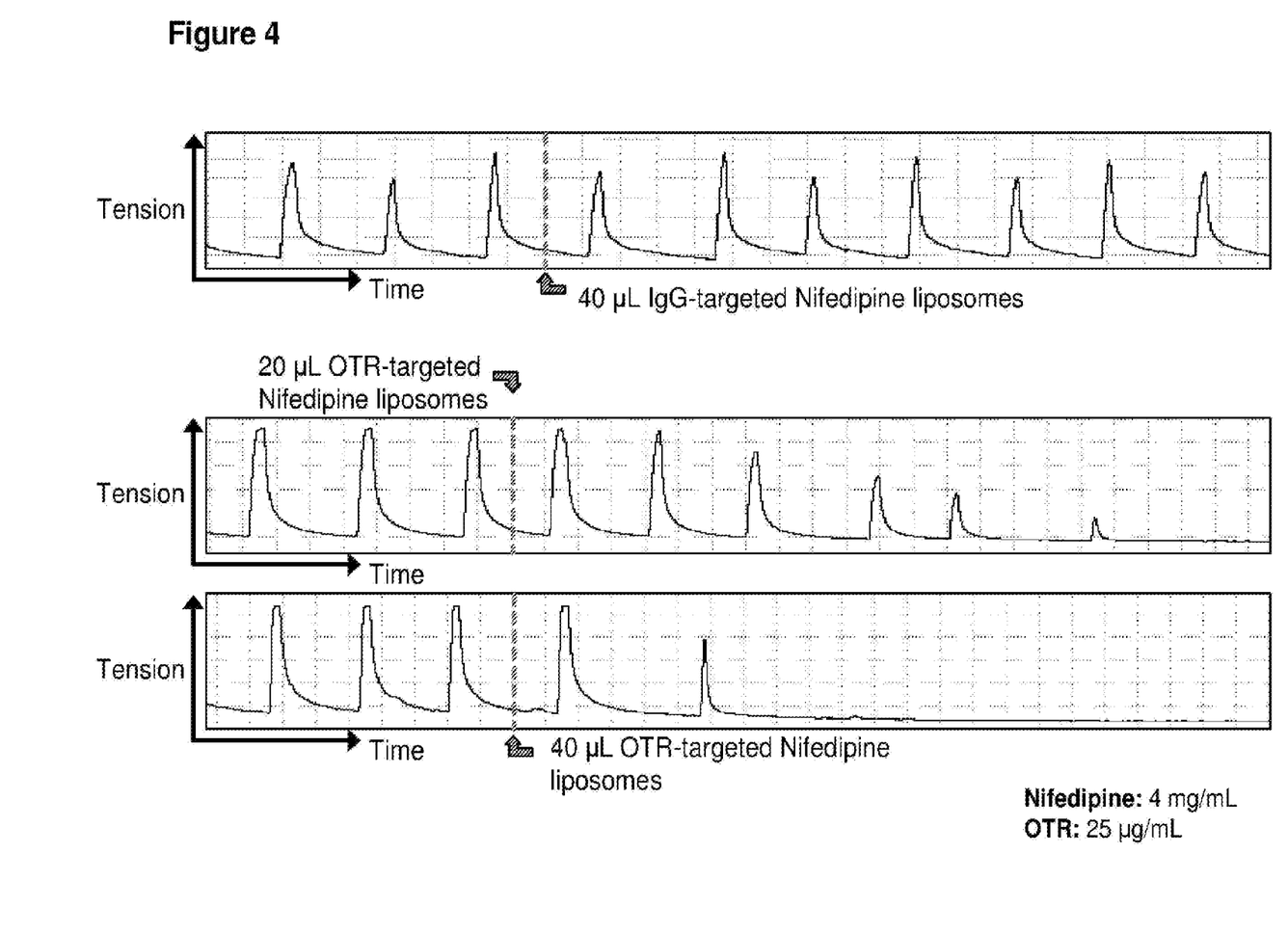
FIG. 4. Time course in spontaneously contracting human myometrial strips treated with: top panel, 40 µL liposomes conjugated with IgG antibodies and loaded with nifedipine (NIF); middle panel, 20 µL liposomes conjugated to anti-oxytocin receptor (OTR) antibodies and loaded with nifedipine; and bottom panel, 40 µL liposomes conjugated to anti-oxytocin receptor (OTR) antibodies and loaded with nifedipine.

Nifedipine-loaded OTR-liposomes were added to spontaneously contracting human myometrial strips and contractility measured. As shown in FIG. 4 (middle and bottom panels), treatment with 20 μl and 40 μl, respectively, of these OTR-targeted liposomes relaxed the myometrial cells, reducing the amplitude of contractions and increasing the time between contractions to the point where contractions ceased. In contrast, treatment with 40 μl dofetilide-loaded IgG-targeted liposomes (FIG. 4, top panel) had no effect on contractility.

Figure 5:
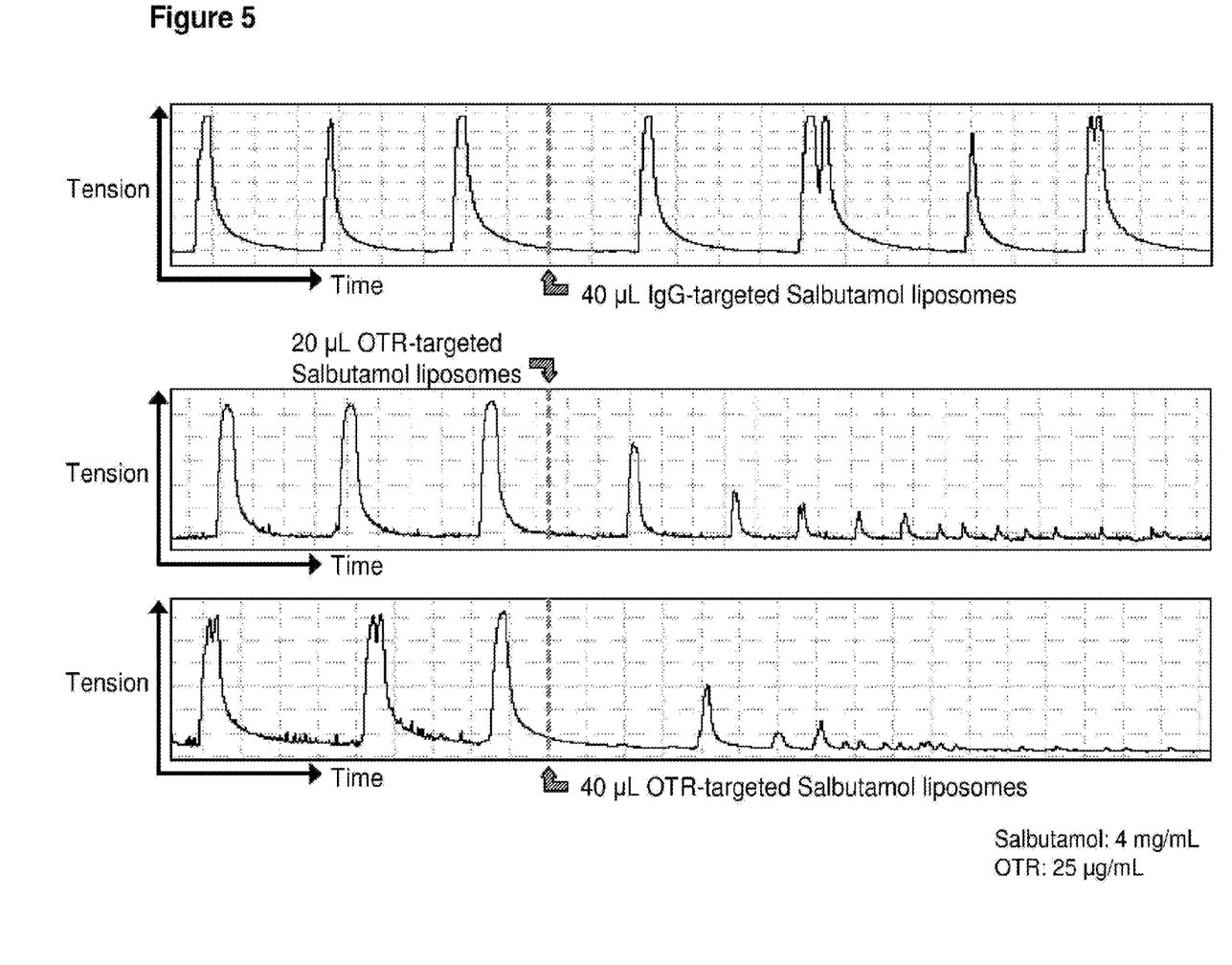
FIG. 5. Time course in spontaneously contracting human myometrial strips treated with: top panel, 40 µL liposomes conjugated with IgG antibodies and loaded with salbutamol (SAL); middle panel, 20 µL liposomes conjugated to anti-oxytocin receptor (OTR) antibodies and loaded with salbutamol; and bottom panel, 40 µL liposomes conjugated to anti-oxytocin receptor (OTR) antibodies and loaded with salbutamol.
Figure 6:
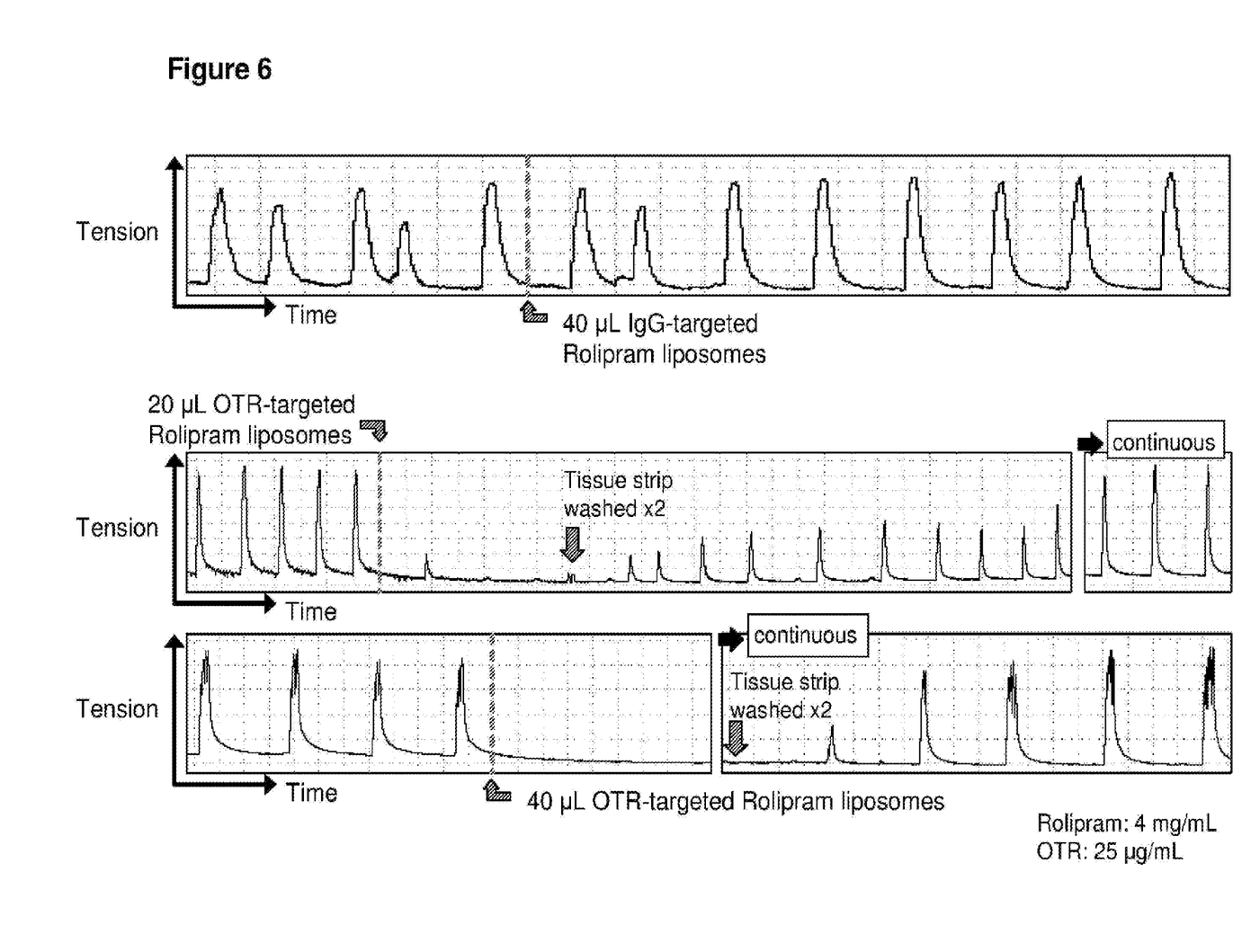
FIG. 6. Time course in spontaneously contracting human myometrial strips treated with: top panel, 40 µL liposomes conjugated with IgG antibodies and loaded with rolipram (ROL); middle panel, 20 µL liposomes conjugated to anti-oxytocin receptor (OTR) antibodies and loaded with rolipram; and bottom panel, 40 µL liposomes conjugated to anti-oxytocin receptor (OTR) antibodies and loaded with rolipram.

Similar results were observed with salbutamol-loaded liposomes (FIG. 5) and rolipram-loaded liposomes (FIG. 6). In the case of rolipram, the inventors also showed that after tissue strips treated with the rolipram-loaded liposomes were washed to remove the liposmes and the drug, contractions resumed and reached the same magnitude (amplitude) as prior to treatment (that is 100% initial contractility was restored, demonstrating that the liposomes do not kill the myocytes) (see FIG. 6, middle and bottom panels).

A summary of the effects of liposomes on myometrial tissue strip contractility as described in Examples 1 and 2 and shown in the Figures, is provided in Table 1.

TABLE 1

Summary of effects of immunoliposome preparations on myometrial contractility

| Immunoliposome preparation[1] | Effect on myometrial tissue |
| --- | --- |
| OTR-targeted liposomes + no drug | No effect |
| Naked liposomes + drug (dofetilide) | No effect |
| IgG-targeted liposomes + dofetilide | No effect |
| OTR-targeted liposomes + dofetilide | Increased contraction duration |
| IgG-targeted liposomes + nifedipine | No effect |
| OTR-targeted liposomes + nifedipine | Relaxation |
| IgG-targeted liposomes + salbutamol | No effect |
| OTR-targeted liposomes + salbutamol | Relaxation |
| IgG-targeted liposomes + rolipram | No effect |
| OTR-targeted liposomes + rolipram | Relaxation |

[1]OTR = oxytocin receptor antibody, IgG = nonspecific IgG that does not target the oxytocin receptor.

Example 3—In Vivo Localisation of Salbutamol-Loaded Liposomes and Effect on Fetal Delivery in Mice In vivo experiments were then carried out to determine the administration of of salbutamol-loaded OTR-liposomes to pregnant mice on fetal delivery.

Preparations of targeted or non-targeted drug-loaded liposomes were administered to pregnant CD1 Swiss mice via lateral tail vein injection as the animals approached term. The total volume for each injection was 100 μL. Liposomes were loaded with salbutamol, and dosage was 3.0 mg/kg/day, administered as daily injections from fetal gestation day 17 (GA17) onwards, until labour occurred. Four mice were injected with non-targeted liposomes containing salbutamol, and four mice were treated with OTR-targeted liposomes containing salbutamol.

Prior to carrying out the in vivo experiments the inventors successfully demonstrated their ability to accurately detect DiI-labelled liposomes using an IVIS 100 imaging system (see below) in vitro in 96-well plates. Fluorescence intensity decreased with decreasing liposome concentration, thereby confirming that the presence of the liposomes could be detected (data not shown).

Upon the completion of labour, mice were euthanized by $CO_2$ asphyxiation and primary organs of interest (brain, uterus, heart, liver, lung, kidney) and fetus were isolated. Organs and fetus were placed on a petri dish in 0.9% saline. The petri dish was then placed inside a Xenogen IVIS 100 unit and imaged under appropriate conditions for the detection of DiI ('DilC18(3)') fluorescence. Imaging parameters were: excitation=554 nm; emission=583 nm;

IVIS Filter set name='DsRed'. Background fluorescence detection was captured and subtracted from all fluorescence images. Liposome localisation appears as fluorescence, and intensity of fluorescence is indicated by a colour scale, where purple denotes low level fluorescence detection whilst red denotes high level fluorescence detection. Matched visible light (no filter) images were captured for each fluorescence image. Results are shown in FIG. 7.

Figure 7:
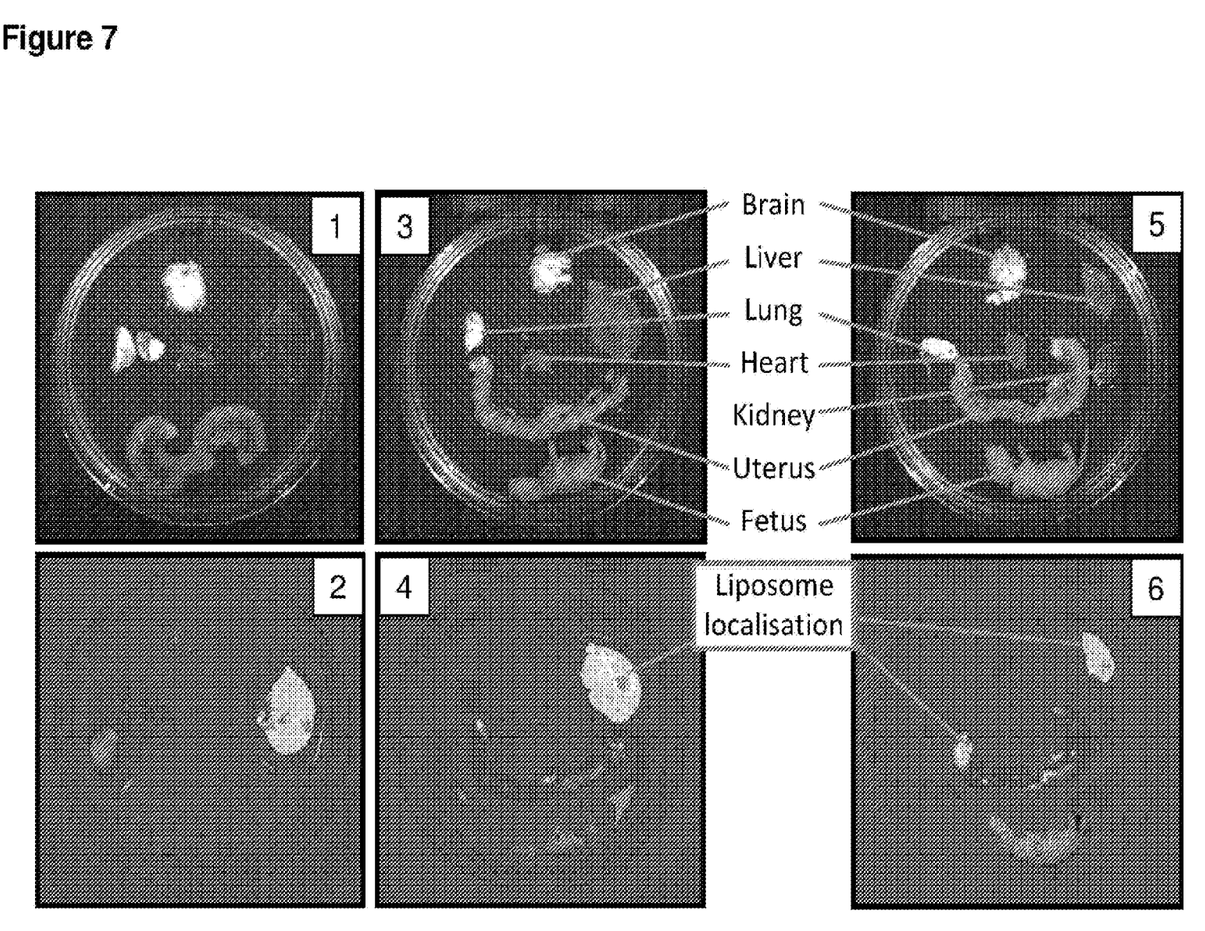
FIG. 7. Liposome localisation following administration of targeted or non-targeted salbutamol-loaded liposomes to pregnant mice approaching labour. Visible light images of maternal organs and fetus (panels 1, 3 and 5) and fluorescence imaging showing liposome localisation (panels 2, 4 and 6). Panels 1 to 4: fetus delivered at fetal gestation day 19. Panels 5 and 6: fetus delivered at gestation day 20.

All mice revealed high levels of liposome localisation in the liver, which is the site of liposome metabolism (FIG. 7 panels 2, 4 and 6). All of the four mice treated with non-targeted liposomes labored at fetal gestation day 19 and revealed no liposome localisation in the uterine tissue, as assessed by IVIS imaging (panel 2). Of the four mice treated with salbutamol-loaded OTR-targeted liposomes only one labored at fetal gestation day 19. This single animal revealed low levels of liposome localisation in the uterine tissue (panel 4). For the three remaining mice treated with salbutamol-loaded OTR-targeted liposomes, labour was delayed by 24 hours until fetal gestation day 20. Analysis of liposome localisation in these animals revealed increased localisation of the OTR-targeted liposomes in the uterine tissue (panel 6).

These results demonstrate that OTR-targeted liposomes are capable of reaching the uterine tissue of pregnant mice, and that the drug carried by the liposomes is capable of exerting an effect on the uterine tissue. In this case the drug being carried by the targeted liposomes, salbutamol, delayed the onset of normal labour in mice by 24 hours at the administered dose of 3.0 mg/kg/day.

REFERENCES

Wildemeersch et al. (2003) Miniature, low-dose, intrauterine drug-delivery systems. *Ann N Y Acad Sci* 997:174-184.

Wildemeersch (2010) Intrauterine drug delivery for contraception and gynecological treatment: novel approaches. *Handb Exp Pharmacol* 197:267-298.

The invention claimed is:

1. A method for targeted delivery to myometrial tissue of one or more agents capable of inhibiting or reducing contractility of said myometrial tissue, comprising exposing myometrial tissue to an effective amount of the one or more agents, wherein the one or more agents are contained or encapsulated within a polymeric delivery vehicle conjugated with anti-oxytocin receptor antibodies or a peptide that binds to the oxytocin receptor,
    wherein the polymeric delivery vehicles containing the agent(s) are administered to a pregnant female mammal, and
    wherein the administration is to slow down labour or prevent premature labour.

2. A method according to claim 1, wherein the polymeric delivery vehicle is a liposome.

3. A method according to claim 1, wherein the polymeric delivery vehicle is coated with anti-oxytocin receptor antibodies or a peptide that binds to the oxytocin receptor.

4. A method according to claim 1, wherein the anti-oxytocin receptor antibodies bind to an extracellular domain of the oxytocin receptor.

5. A method according to claim 1, wherein the one or more agents are selected from calcium channel inhibitors, $\beta_2$-adrenergic receptor agonists and phosphodiesterase inhibitors.

6. A method according to claim 5, wherein the calcium channel inhibitor is nifedipine.

7. A method according to claim 5, wherein the β$_2$-adrenergic receptor agonist is salbutamol or ritodrine.

8. A method according to claim 5, wherein the phosphodiesterase inhibitor is rolipram.

\* \* \* \* \*